United States Patent [19]

Grew et al.

[11] 4,025,520
[45] May 24, 1977

[54] DEHYDROHALOGENATION OF A 7-HALODIHYDROCODEINONE DIALKYL KETAL

[75] Inventors: Edward Leon Grew; Nigel David Vaughan Wilson, both of Edinburgh, Scotland

[73] Assignee: Macfarlan Smith Limited, Edinburgh, Scotland

[22] Filed: Mar. 28, 1975

[21] Appl. No.: 563,052

[30] Foreign Application Priority Data

Apr. 10, 1974 United Kingdom ............ 15971/74

[52] U.S. Cl. .............................................. 260/285
[51] Int. Cl.² ....................................... C07D 489/00
[58] Field of Search .................................. 260/285

[56] References Cited

UNITED STATES PATENTS 2,778,832   1/1957   Gates, Jr. ......................... 260/285

FOREIGN PATENTS OR APPLICATIONS 479,104   7/1929   Germany ......................... 260/285

OTHER PUBLICATIONS

Fieser et al, Reagents for Organic Synthesis, John Wiley & Sons, Inc., N. Y. (1967) pp. 279–281, 298–299.

Rapoport et al., J. Am. Chem. Soc., 89,(8) pp. 1942–1947 (1967).

Primary Examiner—Donald G. Daus
Assistant Examiner—D. G. Rivers
Attorney, Agent, or Firm—Bacon & Thomas

[57] ABSTRACT

A process for the dehydrohalogenation of a 7-halo- or a 1,7-dihalodihydrocodeinone dialkyl ketal of the general formula (I):

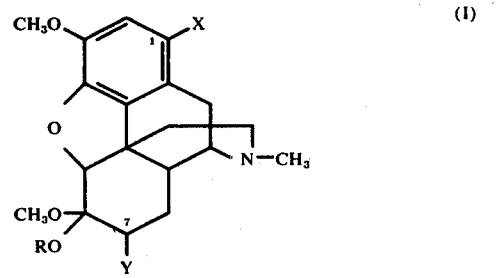

in which R represents an alkyl group containing from 1 to 6 carbon atoms, X represents hydrogen or chlorine or bromine and Y represents chlorine or bromine which comprises subjecting the ketal to the action of a base in the presence of a polar aprotic solvent. The process has utility in facilitating the production of codeine.

13 Claims, No Drawings

DEHYDROHALOGENATION OF A 7-HALODIHYDROCODEINONE DIALKYL KETAL

This invention relates to a novel process for the dehydrohalogenation of certain α-halo ketals some of which are known intermediates in the synthesis of codeine from thebaine.

It is known to prepare 7-bromodihydrocodeinone dimethyl ketal, by treating dihydrothebaine with N-bromoacetamide in methyl alcohol (Rapoport et al J. Amer. Chem. Soc., 1956, 78, 5128; 1967, 89, 1942–47). This α-bromoketal can be dehydrobrominated to the corresponding α:β unsaturated compound, codeinone dimethyl ketal, which on treatment with diluted acetic acid yields codeinone. Codeinone itself is easily reduced to the important analgesic and anti-tussive codeine with a reducing agent, such as sodium borohydride, and it therefore follows that in the attempt to develop a commercially feasible synthetic route to codeine, particularly one which starts from the related opium alkaloid thebaine, the dehydrohalogenation of 7-halodihydrocodeinone dimethyl ketal may well prove to be a key step.

The procedure for dehydrobromination described in the above reference comprises refluxing the α-bromo ketal with potassium tertiary amylate (2-methylbutan-2-oxide) in tertiary amyl alcohol (2-methyl butan-2-ol). This method suffers from certain disadvantages from the commercial point of view, in particular the slowness of the reaction which requires 24 hours to go to completion. Another factor which has to be considered is that the preparation of potassium tertiary amylate involves the use of metallic potassium which is expensive and which, on account of its highly reactive character, is a potentially dangerous substance to handle.

We have found that the use of polar aprotic solvents such as dialkylsulphoxides e.g. dimethyl sulphoxide (DMSO), dialkylformamides, e.g. dimethylformamide (DMF), and cyclic amides, e.g. N-methyl pyrrolidone, dialkylacetamides, e.g. dimethylacetamide (DMA), alkyl phosphoramides e.g. hexamethylphosphoramide, ethers of glycol and polyglycols, such as diglyme (diethyleneglycol dimethyl ether) and sulphones such as sulpholane (tetrahydrothiophene-1,1-dioxide) as solvents for the base catalysed dehydrobromination described above leads to certain advantages. The term "polar aprotic solvent" means a solvent which is not a proton donor and which preferably has a dielectric constant $\epsilon > 15$. Thus with potassium tertiary butoxide as base and DMSO as solvent the reaction proceeds rapidly at room temperature and is complete in about one-half hour, whereas with the same base in boiling tertiary butyl alcohol as solvent the reaction proceeds only to a very small extent (less than 10%) in 24 hours. Furthermore, with DMSO as solvent it is not essential to use potassium tertiary butoxide or potassium tertiary pentoxide for the dehydrobromination and excellent yields of codeinone dimethyl ketal are also obtained using other bases such as alkali metal hydroxides, alkali metal hydrides and alkoxides other than those mentioned above. We have also found that when using an alkali metal hydroxide, the addition of a small amount of water, e.g. up to 20% and particularly 1 to 20% (v/v) is advantageous regard being taken of the fact that some of the solvents specified may be subject to hydrolysis.

It has also been found that the use of DMSO as solvent is similarly effective in promoting the dehydrobromination of 1:7-dibromodihydrocodeinone dimethyl ketal to 1-bromocodeinone dimethyl ketal. The latter can be hydrolysed with dilute acid to 1-bromocodeinone, reduction of which with lithium aluminium hydride yields codeine.

The invention therefore provides a process for the dehydrohalogenation of a 7-halo- or a 1,7-dihalodihydrocodeinone dialkyl ketal of the general formula (I):

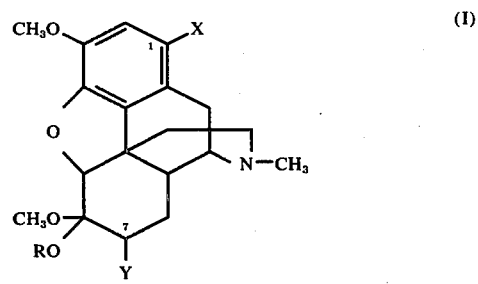

in which R represents an alkyl group containing from 1 to 6 carbon atoms, X represents hydrogen or chlorine or bromine and Y represents chlorine or bromine which comprises subjecting the ketal to the action of a base in the presence of a polar aprotic solvent.

The particularly preferred bases for the reaction according to the invention include alkali metal hydroxides such as sodium or potassium hydroxide or alkali metal hydrides, such as sodium hydride, or alkali metal amides, such as sodamide, or sodium piperidide or alkali metal alkoxides containing 1 to 6 carbon atoms in particular sodium methoxide or ethoxide.

Potassium alkoxides may also be used instead of sodium alkoxides, such as methoxide, ethoxide, butoxide or pentoxide, but these latter bases are less preferred, since the preparation of these reagents involves the use of metallic potassium, which is expensive and potentially dangerous to handle as mentioned above. Particularly, in the preparation of the lower alkoxides using potassium and lower alcohols, a very violent reaction may occur.

The preferred polar aprotic solvent is a dialkyl sulphoxide, preferably a lower dialkyl sulphoxide, in particular dimethyl sulphoxide. Other suitable polar aprotic solvents include those specified above. Preferably the reaction is carried out under substantially anhydrous conditions or when the base is an alkali metal hydroxide the addition of a small amount of water, e.g. up to 20% (v/v) may be advantageous.

In the above general formula I it is preferred that R represents methyl. It is also preferred that X represents hydrogen or bromine.

The ketals in which X is hydrogen, Y is chlorine and R is an alkyl group containing 1 to 6 carbon atoms are novel and the invention includes such ketals as novel compounds. A preferred novel ketal of this type is described in Example 18, namely 7-chlorodihydrocodeinone dimethyl ketal.

According to a preferred feature of the invention, therefore, there is provided a process for the dehydrobromination of 7-bromodihydrocodeinone dimethyl ketal or 1,7-dibromodihydrocodeinone dimethyl ketal which comprises treating said ketal with sodium or potassium hydroxide in the presence of dimethyl sulphoxide as solvent and under anhydrous conditions, or in the presence of a limited amount of water, e.g. up to 20% v/v based on the dimethyl sulphoxide, at a temperature from room temperature to reflux temperature of the solvent and isolating the dehydrobrominated product therefrom. Preferably a temperature of from 70° to 120° C is used when an alkali metal hydroxide is utilized as base.

In carrying out the process of the invention any convenient amount of base may be used but normally a molar excess based on the halo ketal is preferably utilized. In the case of sodium hydride which acts as a very strong base in solvents such as DMSO an excess is, however, preferably to be avoided since this may lead to side reactions.

When utilizing an alkali metal hydroxide an excess of hydroxide based on the compound undergoing dehydrohalogenation is preferably used. Thus, the molar ratio of hydroxide to the halo ketal is preferably greater than 1:1 more particularly 1.5:1 to 10:1, and more particularly 1.5:1 to 4:1.

The invention also provides in a process for the production of codeine from 7-bromodihydrocodeinone dimethyl ketal or 1:7-dibromodihydrocodeinone dimethyl ketal the step of dehydrobrominating said ketal by the method herein described.

It is surprising that the dehydrobromination or dihydrochlorination of the halo ketal takes place with an alkali metal hydroxide and a small amount of water since under the conditions other reactions such as substitution would be expected to take place.

In the production of codeine from dihydrothebaine utilizing the method of the invention there is no necessity to isolate the various intermediates and the process can be operated without such isolation. In particular this is the case using DMSO as solvent, an alkali metal hydroxide as base and utilizing a small amount of water as indicated.

Although the process has in particular been described with relation to dehydrobromination it may also be used for dehydrochlorination.

The ketals used as starting materials may be prepared by the methods generally indicated in Examples 16–18.

The following Examples illustrate the invention.

EXAMPLE 1

Codeinone dimethyl ketal

7-Bromodihydrocodeinone dimethyl ketal (8.48 g) in dimethyl sulphoxide (110 ml) was treated with crushed potassium hydroxide pellets (5.6 g) at room temperature. The mixture was stirred and heated to 80°–90° C in an oil bath and maintained at this temperture for 4½ hours (thin layer chromatography indicated that the dehydrobromination was complete after 3¾ hours). The reaction mixture was cooled to room temperature, diluted well with water and extracted with ether. Evaporation of the ether extract yielded 6.35 g of crude codeinone dimethyl ketal, m.p. 135°–137.5° C (after recrystallization from aqueous methanol).

EXAMPLE 2

Codeinone

The dehydrobromination was carried out as in Example 1 but using 1.76 g of crushed sodium hydroxide pellets in place of the potassium hydroxide. Thin layer chromatography indicated that the reaction was complete after 4½ hours. Instead of isolating the codeinone dimethyl ketal as in Example 1, the reaction mixture was cooled to room temperature and treated with N hydrochloric acid (74 ml) to hydrolyse the ketal. After stirring at room temperature for 1¼ hours the mixture was poured into ice-water (25 ml) containing a slight excess of ammonia. The precipitate of codeinone which separated was filtered off, washed with water and dried at 50° C. Yield 4.91 g m.p. 179°–182.5° C (after recrystallization from ethyl acetate).

EXAMPLE 3

1-Bromocodeinone dimethyl ketal

A mixture of 1:7-dibromodihydrocodeinone dimethyl ketal (5.03 g) and potassium tertiary butoxide (5.60 g) was treated with dimethyl sulphoxide (30 ml) and the mixture stirred at room temperature for 1½ hours (thin layer chromatography showed that the dehydrobromination was complete after 30 minutes). The reaction mixture was then added slowly to ice-water (300 ml) and the precipitate of 1-bromocodeinone dimethyl ketal which separated was filtered off, washed with water and dried at 50° C. Yield 2.95 g m.p. 123°–124° C (after recrystallization from alcohol).

A similar experiment was carried out for purposes of comparison using tertiary butyl alcohol as solvent at reflux temperature (82.8° C) in place of dimethyl sulphoxide at room temperature. Thin layer chromatography showed that the dehydrobromination proceeded only very slowly under these conditions and was less than 10% complete after 24 hours.

EXAMPLE 4

1-Bromocodeinone dimethyl ketal

1:7-Dibromodihydrocodeinone dimethyl ketal (10 g) and crushed potassium hydroxide pellets (5.6 g) were stirred with dimethyl sulphoxide (65 ml) and heated to 70°–80° C. Thin layer chromatography showed that the dehydrobromination was complete after 3 hours. The reaction mixture was cooled, diluted well with water and extracted with ether. Evaporation of the ether extract gave 5.34 g of 1-bromocodeinone dimethyl ketal, m.p. 121°–124° C (after recrystallisation from alcohol).

EXAMPLE 5

1-Bromocodeinone

1:7-Dibromohydrocodeinone dimethyl ketal (22.56 g) and crushed sodium hydroxide pellets (5.28 g) were stirred with dimethyl sulphoxide (330 ml) at 70°–80° C. Thin layer chromatography showed that little reaction had occurred after 1½ hours. Water (6.6 ml) was then added and the reaction mixture examined by thin layer chromatography after a further 1¼ hours heating at 70°–80° C when it was found that the dehydrobromination had proceeded to the extent of about 50%. Thereafter the reaction slowed down and almost ceased. A further 6.6 ml of water was therefore added, following which the reaction restarted and was found to be virtually complete after 6¼ hours heating at 70°–80° C. The reaction mixture was cooled and poured with stirring into three volumes of cold water. The precipitated 1-bromocodeinone dimethyl ketal was filtered off, washed with water and sucked as dry as possible. The damp solid was hydrolysed by dissolving in 2N hydrochloric acid (110 ml) and stirring at room temperature for 2½ hours. The resulting 1-bromocodeinone was isolated by pouring the solution into ice-water (400 ml) containing a small excess of ammonia, filtering off the precipitated solid, washing the latter well with water and drying at 50° C. Yield 11.5 g m.p. 191°–192.5° C (after recrystallisation from methanol).

EXAMPLE 6

Codeine

If desired, 7-bromodihydrocodeinone dimethyl ketal can be converted to codeine without isolating the intermediate products codeinone dimethyl ketal and codeinone.

7-Bromodihydrocodeinone dimethyl ketal (84.8 g) and pearl sodium hydroxide (17.64 g) were stirred together at 90° – 100° C in dimethyl sulphoxide (175 ml) containing 5% (v/v) of water. The dehydrobromination reaction was followed by thin layer chromatography and appeared to be complete after about 3 hours. After heating for a further period of 1 hour at the same temperature the hot reaction mixture was poured slowly with good stirring into water (500 ml) at 0.° C. The crude codeinone dimethyl ketal which separated was hydrolysed, without being isolated, by adding 2N sulphuric acid (230 ml) to the reaction mixture at 20° C and stirring for 1 hour, when thin layer chromatography showed conversion to codeinone to be complete.

Crude codeinone sulphate crystallised out from the solution at the end of the hydrolysis as a beige solid which was not isolated. The reaction mixture was rendered alkaline by the addition of 2N sodium hydroxide (120 ml) and methanol (200 ml) and an equal volume of water were added, followed by sodium borohydride (3.8 g) added portionwise over 15 minutes while keeping the reaction temperature at 20° C by external cooling. After stirring the reaction mixture for 1½ hours thin layer chromatography showed the reduction of codeinone to codeine to be complete.

The reaction mixture was extracted several times with chloroform (6 × 200 ml) and the combined solvent extracts then washed once with water (200 ml) and shaken with 1N hydrochloric acid. (3 × 100 ml). The aqueous acid extracts were combined, basified with ammonium hydroxide to pH 9, re-extracted with chloroform (300 ml, 200 ml, 2 × 100 ml), and the chloroform extracts dried over sodium sulphate. Removal of the solvent in vacuo gave crude codeine base (57.12 g).

The crude base (56.5 g) was dissolved in 74 o.p. spirit (81 ml) and water (100 ml) and the solution filtered and treated with 50% v/v aqueous sulphuric acid to give a pH of ca 4.5 (10.9 ml). The solution was cooled to ca 5° C and the codeine sulphate which crystallised out filtered off and washed with ice-cold 50% aqueous alcohol. The product was dried at 50° C to constant weight to give anhydrous codeine sulphate (56.36 g). The material assayed 99.6% pure by non-aqueous titration and gave codeine alkaloid, m.p. 155.5° C on basification with excess ammonia.

EXAMPLE 7

Codeinone

7-Bromodihydrocodeinone dimethyl ketal (2.12 g) was stirred in hexamethylphosphoramide (10 ml) at room temperature and treated with solid potassium tertbutoxide (1.23 g). Thin layer chromatography indicated that the dehydrobromination was complete after 1¼ hours. The reaction mixture was poured with stirring into cold water (75 ml) and the precipitated codeinone dimethyl ketal was extracted with chloroform (3 × 20 ml). The combined chloroform solutions were extracted with N/4 sulphuric acid (20, 2 × 5 ml) and the resulting solution left at 20° C for 1 hour in order to complete the hydrolysis (during this period some codeinone sulphate separated as white needles). The mixture was then cooled in an ice/water bath and basified with stirring by addition of a solution of sodium hydroxide (0.4 g) in water (5 ml). Codeinone separated as a fine, white solid which was filtered off, washed twice with ice-cold water, and dried under vacuum at room temperature. Yield 1.38 g m.p. 179°–183° C (after recrystallisation from ethyl acetate).

EXAMPLE 8

Codeinone

A solution of 7-bromodihydrocodeinone dimethyl ketal (2.12 g) in N,N-dimethylformamide (20 ml) was stirred at room temperature and treated with solid potassium tert-butoxide (1.23 g). Thin layer chromatography showed that the reaction was complete after 4½ hours. The reaction solution was poured into cold water (150 ml) and extracted with chloroform (3 × 20 ml). The combined chloroform solutions were extracted with N/3 sulphuric acid (2 × 15 ml) and the acid extracts left at room temperature for 2 hours and then washed with chloroform (2 × 20 ml). Basification with a slight excess of ammonia and chloroform extraction (2 × 20, 10 ml), followed by drying of the extracts over sodium sulphate and solvent removal in vacuo, gave 1.44 g of a crystalline residue of crude codeinone m.p. 183.5° – 186.5° C (after recrystallisation from ethyl acetate).

EXAMPLE 9

Codeinone

A solution of 7-bromodihydrocodeinone dimethyl ketal (2.12 g) in N,N-dimethylacetamide (20 ml) was stirred at room temperature and treated with solid potassium tert-butoxide (1.23 g). The dehydrobromination was observed to be complete after 1 hour (t.l.c.). The reaction mixture was diluted with water (150 ml) and worked up as in the case of dimethylformamide (Example 8) to give 1.29 g of codeinone m.p. 181° – 185° C (after recrystallisation from ethyl acetate).

EXAMPLE 10

Codeinone dimethyl ketal

7-Bromodihydrocodeinone dimethyl ketal (4.24 g) and sodium hydride (0.5 g. 50% dispersion in oil) were stirred in calcium hydride dried dimethyl sulphoxide (20 ml) at 90° C. Dehydrobromination was complete after approximately 6 hours (t.l.c.). The hot reaction mixture was poured slowly with stirring into ice-cold water (50 ml) and the precipitated codeinone dimethyl ketal was filtered off, washed with water (20 ml) and dried under vacuum at 25° C. Yield 2.87 g. m.p. 133°–136.5° C (after recrystallisation from 2 : 1 v/v methanol : water).

EXAMPLE 11

1-Bromocodeinone 1,7-Dibromodihydrocodeinone dimethyl ketal (2.52 g) was stirred in dimethyl sulphoxide (25 ml) at room temperature with sodium ethoxide (0.75 g). The dehydrobromination was virtually complete after 3 hours, but stirring was continued overnight. After 21 hours the reaction mixture was poured slowly with stirring into ice-cold water (75 ml), and the resulting precipitate was filtered off and washed with water. The damp material was dissolved in N hydrochloric acid (15 ml) and stirred at 20° C for 3 hours. This acid solution was then poured slowly with stirring into ice cold water (50 ml) containing a slight excess of ammonia, and the precipitated 1-bromocodeinone was filtered off, washed with water and dried at 50° C. Yield 1.0 g m.p. 187° – 189° C (after recrystallisation from methanol).

EXAMPLE 12

Codeinone dimethyl ketal

7-Bromodihydrocodeinone dimethyl ketal (2.12 g) and solid potassium tert-butoxide (1.23 g) were stirred in sulpholane (10 ml) and heated at 50° C. Thin layer chromatography indicated that the reaction was complete after 3¾ hours. The reaction mixture was added slowly with stirring to ice-cold water (100 ml) and the precipitated codeinone dimethyl ketal was filtered off, washed with water and dried under vacuum at 40° C. Yield 1.32 g m.p. 133° –138° C (after recrystallisation from 2:1 v/v methanol:water).

EXAMPLE 13

Codeinone dimethyl ketal

7-Bromodihydrocodeinone dimethyl ketal (2.12 g) and solid potassium tert-butoxide (1.23 g) were stirred in diglyme (12.5 ml) and heated at 55°–60° C. Thin layer chromatography showed that reaction was complete after 2½ hours. The hot reaction mixture was then added slowly with stirring to ice-cold water (110 ml) and the resulting precipitate of codeinone dimethyl ketal was filtered off, washed with water and dried under vacuum at 30° C. Yield 1.36 g m.p. 136°–138° C (after recrystallisation from 2:1 v/v methanol:water).

EXAMPLE 14

Codeinone

Sodium hydride (1.04 g of a 50% dispersion in oil) was stirred with piperidine (3.4 g) at room temperature under dry nitrogen. After 5 minutes the excess piperidine was removed under reduced pressure to give a light grey residue of sodium piperidide. 7-Bromodihydrocodeinone dimethyl ketal (4.24 g) and hexamethylphosphoramide (20 ml) were then added and the mixture was stirred and heated at 90° C. The dehydrobromination was found to be complete after approximately 3 hours (t.l.c.). The hot reaction solution was then poured slowly with stirring into water (70 ml) at 5° C and the precipitate of codeinone dimethyl ketal was extracted into chloroform (3 × 20 ml). The combined chloroform solutions were extracted with 1N sulphuric acid (10, 2 × 5 ml) and the acid extracts stirred at room temperature for 1½ hours to ensure complete hydrolysis. During this period, codeinone sulphate separated as a white crystalline solid. The slurry was cooled to 5° C and treated dropwise with a solution of sodium hydroxide (0.8 g) in water (5 ml), after which the precipitate of codeinone was filtered off, washed with water and dried in a vacuum oven at 30° C. Yield 2.16 g m.p. 178°–184° C (after recrystallisation from ethyl acetate).

EXAMPLE 15

Codeinone dimethyl ketal

7-Bromodihydrocodeinone dimethyl ketal (4.24 g) and sodamide (0.86 g) were stirred in hexamethylphosphoramide (15 ml) and heated at 85°–90° C. The reaction was estimated to be complete by t.l.c. after 4 hours and the hot reaction solution was then added dropwise with stirring to ice-cold water (100 ml) in order to precipitate the codeinone dimethyl ketal. The product was filtered off, washed with water and dried in a vacuum oven at 30° C. Yield 1.66 g m.p. 136°–139° C (after crystallisation from methanol).

EXAMPLE 16

Codeinone

A solution of 7-bromodihydrocodeinone methyl n-propyl ketal (9.02 g) in warm 19:1 v/v dimethyl sulphoxide:water (17.5 ml) was treated with pearl sodium hydroxide (1.76 g) and the mixture stirred and heated at 90°–100° C. The dehydrobromination was found to be complete by t.l.c. after 4 hours. After cooling to 15° C, the reaction mixture was stirred and acidified by addition of 2N sulphuric acid (23 ml) and stirring was maintained at room temperature for 2 hours, by which time the hydrolysis was complete. The reaction solution was then basified by addition with cooling of a solution of sodium hydroxide (1.6 g) in water (5 ml) and the resulting mixture was extracted with chloroform (3 × 20 ml). The combined chloroform extracts were washed with water (25 ml), dried over sodium sulphate, and solvent removed under reduced pressure to give a brown residue which was crystallised from ethyl acetate to give codeinone (2.15 g) m.p. 179°–184° C.

The starting material was prepared as follows:

Preparation of 7-bromodihydrocodeinone methyl n-propyl ketal

Dihydrothebaine (6.26 g) and p-toluenesulphonic acid monohydrate (3.80 g) were stirred in n-propanol (35 ml) at room temperature to produce a slurry of dihydrothebaine p-toluenesulphonate. A solution of 1,3-dibromo-5,5-dimethylhydantoin (2.95 g) in acetone (20 ml) was then added dropwise over ½ hour and stirring was maintained for a further ½ hour. The reaction solution was then added with stirring to a solution of sodium hydroxide (1.6 g) in water (180 ml) at 5° C. This precipated the product as a white, sticky solid which was unsuitable for filtration and the material was therefore extracted into chloroform (30, 25 ml). The combined chloroform extracts were washed with water (30 ml), dried over sodium sulphate and solvent removed under reduced pressure to give crude 7-bromodihydrocodeinone methyl n-propyl ketal (9.02 g) as a brown gum, which was used without purification for the dehydrobromination stage.

EXAMPLE 17

Codeinone

7-Bromodihydrocodeinone methyl n-pentyl ketal (2.5 g) and potassium tert-butoxide (1.46 g) were stirred in dimethyl sulphoxide (20 ml) at about 35° C. Examination by t.l.c. showed that the dehydrobromination was complete after 2 hours. The reaction solution was then diluted with water (100 ml), extracted with chloroform (6 × 20 ml) and the combined chloroform extracts washed with water (20 ml) and re-extracted with N/4 sulphuric acid (2 × 20, 2 × 10 ml). The hydrolysis was complete after approximately 1 hour at room temperature and the acidic solution was basified with ammonia to pH 9 and extracted with chloroform (3 × 40 ml). After drying the extracts over sodium sulphate, the solvent was removed under reduced pressure to give a crystalline residue of codeinone. Yield 0.95 g m.p. 180°–185° C (after crystallisation from ethyl acetate). The i.r. spectrum of the product was identical with that of an authentic codeinone sample.

The starting material was prepared as follows:

Preparation of 7-bromodihydrocodeinone methyl n-pentyl ketal

Dihydrothebaine (6.26 g) and p-toluenesulphonic acid monohydrate (3.8 g) were stirred in n-pentanol (20 ml) at 21° C and the resulting slurry was treated dropwise over ½ hour with a solution of 1,3-dibromo-5,5-dimethylhydantoin (2.95 g) in acetone (19 ml). Stirring was maintained for a further ½ hour and the reaction solution was filtered to remove some white solid, which was found to be mainly unreacted dihydrothebaine p-toluenesulphonate. The filtrate was concentrated under reduced pressure to a volume of 20 ml, toluene (20 ml) was added and the solution was washed with N/2 sulphuric acid (17 ml). The organic solution was then washed with water (20 ml), dried over sodium sulphate and solvent removed under reduced pressure to give crude 7-bromodihydrocodeinone methyl n-pentyl ketal (7.18 g) as a brown gum. This material was purified by column chromatography on silica (Sorbsil eluted with up to 5% methanol in chloroform) prior to dehydrobromination.

EXAMPLE 18

Codeinone

7-Chlorodihydrocodeinone dimethyl ketal (7.66 g) and pearl sodium hydroxide (1.76 g) were stirred with 19:1 v/v. dimethyl sulphoxide:water (17.5 ml) and the mixture heated at 90°–100° C. T.l.c. indicated that the reaction was complete after about 16 hours, and the reaction mixture was then poured with stirring into ice-cold water (70 ml). The mixture was extracted with chloroform (3 × 20 ml) and the combined extracts were washed with water (25 ml). The chloroform solution was extracted with 1N sulphuric acid (20 , 2 × 5 ml) and the combined acid solutions were stirred at 20° C for 1 hour. Stirring was maintained and the mixture was cooled to 5° C and basified by addition of a solution of sodium hydroxide (1.6 g) in water (5 ml). Extraction with chloroform (3 × 20 ml) followed by a water wash (25 ml), drying over sodium sulphate, removal of solvent under reduced pressure and recrystallisation of the residue from ethyl acetate gave codeinone, m.p. 177°–180° C, the identity of which was confirmed by comparison of the i.r. and n.m.r. spectra with those of an authentic sample of the base.

The starting material was prepared as follows:

Preparation of 7-chlorodihydrocodeinone dimethyl ketal

Dihydrothebaine (6.26 g) and p-toluenesulphonic acid monohydrate (3.80 g) were dissolved with stirring in methanol (40 ml) at 17° C. A solution of 1,3-dichloro-5,5-dimethylhydantoin (3.98 g) in acetone (45 ml) was added dropwise over 1 hour and stirring was continued for a further ½ hour. Examination of a reaction sample at this stage by t.l.c. showed that the chlorination was virtually complete. Solvent was removed under reduced pressure and the residue was partitioned between toluene (20 ml) and a solution of sodium hydroxide (1.6 g) in water (20 ml) at 35° C. After separation of the phases, the aqueous fraction was re-extracted with toluene (20, 2 × 10 ml) and the combined toluene extracts were dried over sodium sulphate and solvent removed under reduced pressure to give crude 7-chlorodihydrocodeinone dimethyl ketal (7.66 g) as a yellow gum. The product was used without further purification for the dehydrochlorination stage.

EXAMPLE 19

Codeinone

7-Bromodihydrocodeinone dimethyl ketal (2.12 g) and pearl sodium hydroxide (2.0 g) were stirred in hexamethylphosphoramide (10 ml) and heated at 95° C. Thin layer chromatography indicated that the dehydrobromination was complete after approximately 1 hour. The hot reaction mixture was cooled to room temperature, poured with stirring into water (100 ml) at 15° C and the resulting precipitate of codeinone dimethyl ketal was extracted with chloroform (3 × 20 ml). The combined extracts were then washed with water (20 ml), extracted with N/4 sulphuric acid (20, 2 × 5 ml) and the acid solution stirred at 20° C for 1¼ hours in order to complete the hydrolysis (during this time some codeinone sulphate crystallised as white needles). The mixture was then cooled in an ice/water bath and basified with stirring by slow addition of a solution of sodium hydroxide (0.4 g) in water (5 ml). Codeinone separated as a fine, white solid which was filtered off, washed with cold water (2 × 5 ml) and dried under vacuum at 40° C. Yield 1.38 g m.p. 176°–182° C (after recrystallization from ethyl acetate). The product was identical by t.l.c. and i.r. with an authentic sample of codeinone.

EXAMPLE 20

Codeinone

7-Bromodihydrocodeinone dimethyl ketal (2.12 g) and pearl sodium hydroxide (2.0 g) were stirred in N,N-dimethylformamide (25 ml) and heated at 120° C. Examination by t.l.c. showed that the dehydrobromination was complete after approximately 10 hours. The reaction mixture was then cooled to room temperature and added with stirring to water (150 ml) at 0° C. The precipitate of codeinone dimethyl ketal was extracted into chloroform (3 × 20 ml) and the combined extracts were washed with water (30 ml). The ketal was then hydrolysed by extracting into N/3 sulphuric acid (2 × 15 ml) and stirring the acidic solution at room temperature. (Small white needles of codeinone sulphate soon began to form). After 1½ hours the mixture was cooled using an ice/water bath and was basified with stirring by slow, dropwise addition of a solution of sodium hydroxide (0.4 g) in water (5 ml). Codeinone formed as a fine white solid which was filtered off, washed with cold water and dried under vacuum at 30° C. Yield 1.04 g m.p. 180°–184° C (after recrystallization from ethyl acetate).

We claim:

1. A process for the dehydrohalogenation of a 7-halo- or a 1,7-dihalodihydrocodeinone dialkyl ketal of the general formula (I):

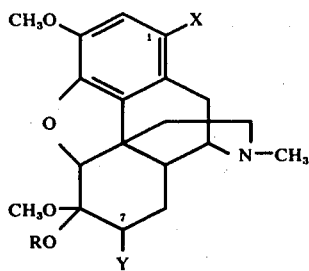

in which R represents an alkyl group containing from 1 to 6 carbon atoms, X represents hydrogen or chlorine or bromine and Y represents chlorine or bromine which comprises subjecting the ketal to the action of an alkali metal hydroxide in the presence of a polar aprotic solvent which is not a proton donor and which has a dielectric constant $\epsilon > 15$.

2. A process as claimed in claim 1 in which the base is sodium or potassium hydroxide.

3. A process as claimed in claim 1 in which the solvent is a lower dialkyl sulphoxide.

4. A process as claimed in claim 6 in which the dialkylsulphoxide is dimethylsulphoxide.

5. A process as claimed in claim 1 in which the solvent is a di(lower alkyl)formamide, a di(lower alkyl)acetamide, an alkyl phosphoramide, a glycol ether or polyglycol ether or a sulphone.

6. A process as claimed in claim 1 in which the dialkyl ketal is a dimethyl ketal.

7. A process as claimed in claim 1 in which X is hydrogen or bromine.

8. A process as claimed in claim 1 in which an alkali metal hydroxide is used as base, the solvent is dimethylsulphoxide and the reaction is carried out in the presence of up to 20% of water (v/v).

9. A process as claimed in claim 11 in which a molar ratio of alkali metal hydroxide to halo ketal of from 1.5:1 to 10:1 is used.

10. A process as claimed in claim 1 in which the reaction is effected at a temperature within the range of room temperature to the reflux temperature of the solvent.

11. A process for the dehydrobromination of 1:7-dibromodihydrocodeinone dimethyl ketal or 7-bromodihydrocodeinone dimethyl ketal, in which said ketal is contacted with an alkali metal hydroxide and dimethyl sulphoxide in the presence of up to 20% water (v/v) based on the dimethyl sulphoxide, the molar ratio of alkali metal hydroxide to dimethyl sulphoxide being from 1.5:1 to 10:1 at an elevated temperature.

12. A process as claimed in claim 11 in which a temperature within the range of 70° to 120° C is used.

13. In a process for the preparation of codeine from dihydrothebaine by the steps of:
 a. preparing a 7-halo- or 1,7-dihalodihydrocodeinone dialkyl ketal as defined in claim 1;
 b. dehydrohalogenating said 7-halo- or 1,7-dihalodihydrocodeinone to produce the corresponding codeinone ketal;
 c. hydrolysing said codeinone ketal or 1-halocodeinone ketal from step (b);
 d. reducing the codeinone or 1-halocodeinone from step (c); and
 e. recovering codeine, the improvement which consists of carrying out step (b) by dehydrohalogenating a 7-halo- or a 1,7-dihalodihydrocodeinone dialkyl ketal of the general formula (I):

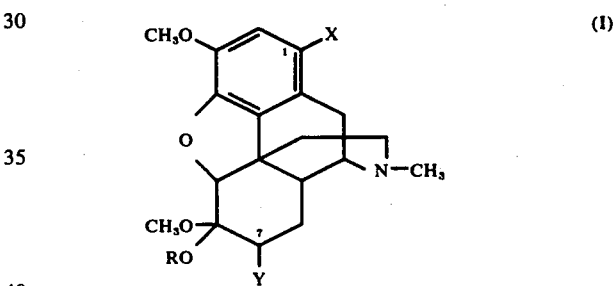

in which R represents an alkyl group containing from 1 to 6 carbon atoms, X represents hydrogen or chlorine or bromine and Y represents chlorine or bromine by subjecting the ketal to the action of an alkali metal hydroxide in the presence of a polar aprotic solvent which is not a proton donor and which has a dielectric constant $\epsilon > 15$.

* * * * *